United States Patent
Shin et al.

(10) Patent No.: US 10,618,027 B2
(45) Date of Patent: Apr. 14, 2020

(54) METHOD FOR DECOLORING IONIC LIQUID

(71) Applicant: INDUSTRY-ACADEMIC COOPERATION FOUNDATION CHOSUN UNIVERSITY, Gwangju (KR)

(72) Inventors: Dong-Chan Shin, Gwangju (KR); Ki-Hyun Kim, Gwangju (KR); Yong-Taeg Oh, Jeollanam-do (KR)

(73) Assignee: INDUSTRY-ACADEMIC COOPERATION FOUNDATION CHOSUN UNIVERSITY, Gwangju (KR)

( * ) Notice: Subject to any disclaimer, the term of this patent is extended or adjusted under 35 U.S.C. 154(b) by 35 days.

(21) Appl. No.: 16/067,339

(22) PCT Filed: Feb. 14, 2017

(86) PCT No.: PCT/KR2017/001616
§ 371 (c)(1),
(2) Date: Jun. 29, 2018

(87) PCT Pub. No.: WO2017/150822
PCT Pub. Date: Sep. 8, 2017

(65) Prior Publication Data
US 2019/0009243 A1    Jan. 10, 2019

(30) Foreign Application Priority Data

Feb. 29, 2016 (KR) ........................ 10-2016-0024177

(51) Int. Cl.
*B01J 19/12* (2006.01)
*B01D 17/00* (2006.01)
(Continued)

(52) U.S. Cl.
CPC ............ *B01J 19/123* (2013.01); *B01D 17/00* (2013.01); *C07C 311/03* (2013.01);
(Continued)

(58) Field of Classification Search
CPC .............. B01J 19/123; B01J 2219/1203; B01J 2219/0877; C07D 233/58; C07C 311/03; B01D 17/00
(Continued)

(56) References Cited

U.S. PATENT DOCUMENTS 3,330,747 A * 7/1967 Moore ................. C07D 471/04
204/157.72
2007/0095647 A1* 5/2007 Dundore ................ B01J 35/004
204/157.15

(Continued)

FOREIGN PATENT DOCUMENTS

JP    06-055768 B2    7/1994
KR    10-0729500 B1    6/2007
(Continued)

OTHER PUBLICATIONS

Asaka et al, "Photochromism of 3-butyl-1-methyl-2-phenylazoimidazolium in room temperature ionic liquids," Journal of Photochemistry and Photobiology A: Chemistry 209 (2010) 12-18 (Year: 2010).*
(Continued)

*Primary Examiner* — Nicholas A Smith
*Assistant Examiner* — Colleen M Raphael
(74) *Attorney, Agent, or Firm* — The PL Law Group, PLLC

(57) ABSTRACT

A method of decoloring an ionic liquid includes preparing a discolored ionic liquid, and decoloring the discolored ionic liquid through irradiation with UV rays. An ionic liquid that is discolored due to heat treatment upon purification is
(Continued)

decolored and can thus be reused. The method of decoloring the ionic liquid is effective because an ionic liquid, which is discolored due to heat treatment upon purification, can be decolored in a simple manner and also because an ionic liquid, which is discolored and is thus difficult to apply to the purification of an organic material, can be decolored in a simple manner, and can thus be reused in the form of a high-purity ionic liquid.

6 Claims, 4 Drawing Sheets

(51) Int. Cl.
    *C07C 311/03*     (2006.01)
    *C07D 233/58*     (2006.01)
(52) U.S. Cl.
    CPC ..... *C07D 233/58* (2013.01); *B01J 2219/0877* (2013.01); *B01J 2219/1203* (2013.01)
(58) Field of Classification Search
    USPC ........................................ 204/157.52, 157.72
    See application file for complete search history.

(56) References Cited

U.S. PATENT DOCUMENTS

| | | | | |
|---|---|---|---|---|
| 2012/0130111 | A1* | 5/2012 | Koh | C07C 68/00 558/277 |
| 2017/0247729 | A1* | 8/2017 | Liszka | C08H 8/00 |
| 2018/0346938 | A1* | 12/2018 | Xu | C12P 7/10 |
| 2019/0016860 | A1* | 1/2019 | Searcy | B01J 19/123 |

FOREIGN PATENT DOCUMENTS

| | | |
|---|---|---|
| KR | 10-1542346 B1 | 8/2015 |
| KR | 10-1551890 B1 | 9/2015 |

OTHER PUBLICATIONS

Cremer et al, "Towards a Molecular Understanding of Cation-Anion Interactions—Probing the Electronic Structure of Imidazolium Ionic Liquids by NMR Spectroscopy, X-ray Photoelectron Spectroscopy and Theoretical Calculations." Chem. Eur. J. 2010, 16, 9018-9033 (Year: 2010).*
Cvjetko, Marina, and Polona Žnidaršič-Plazl. "Ionic liquids within microfluidic devices," in Ionic liquids: theory, properties, new approaches. IntechOpen, 2011. (Year: 2011).*
Kawai et al, "Photochromic Reaction of a Novel Room Temperature Ionic Liquid: 2-Phenylazo-1-hexyl-3-methylimidazolium Bis(pentafluoroethylsulfonyl)amide," Chem. Lett. 2010, 39, 230231 (Year: 2010).*
Wang et al, "Towards understanding the color change of 1-butyl-3-methylimidazolium bis(trifluoromethylsulfonyl)imide during gamma irradiation: an experimental and theoretical study," Phys.Chem. Chem.Phys., 2014, 16, 18729 (Year: 2014).*
International Search Report for PCT/KR2017/001616 dated Jun. 14, 2017.
Yuan, L. et al., "Radiation-induced Darkening of Ionic Liquid [C4min][NTf2] and Its Decoloration", Radiation Physics and Chemistry, vol. 78, No. 12, pp. 1133-1136, 2009. See pp. 1133-1136.
Office action dated May 26, 2017 from Korean Patent Office in a counterpart Korean Patent Application No. 10-2016-0024177 (all the cited references are listed in this IDS.) (English translation is also submitted herewith.).

* cited by examiner

FIG.2

METHOD FOR DECOLORING IONIC LIQUID

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2017/001616, filed Feb. 14, 2017, which claims priority to the benefit of Korean Patent Application No. 10-2016-0024177 filed in the Korean Intellectual Property Office on Feb. 29, 2016, the entire contents of which are incorporated herein by reference.

TECHNICAL FIELD

The present invention relates to a method of decoloring an ionic liquid, and more particularly to a method of decoloring an ionic liquid, in which an ionic liquid that is discolored due to heat treatment upon purification is decolored and may thus be reused as a high-purity ionic liquid.

BACKGROUND ART

An ionic liquid is a salt composed of an organic cation of a hetero ring and an inorganic anion. Although NaCl, a representative inorganic salt, has to be melted at a temperature of 800° C. or higher, an ionic liquid typically has a low melting point of 100° C. or less.

An ionic liquid is less toxic than general organic solvents, and has almost no vapor pressure, and is thus non-volatile. Moreover, an ionic liquid may efficiently dissolve inorganic and organic chemicals because of the strong polarity thereof, and is thus receiving attention as a green solvent capable of replacing organic solvents. Ionic liquids have high ionic conductivity, a wide electrochemical range, and high thermal stability. By virtue of the superior properties thereof, ionic liquids have been utilized in a variety of fields, including those of secondary battery electrolytes, catalysts, liquid-liquid extraction solvents, carbon dioxide capture, thermal fluids, etc. Furthermore, ionic liquids are advantageous because the properties of the ionic liquids may vary depending on changes in the size and structure of cations and anions, making it possible to design an ionic liquid so as to be suitable for an industrial-processing end use through various combinations of two ions. Hence, thorough research thereon by institutes and companies is ongoing.

Recently, a high-purity ionic liquid is used to purify a material such as an organic material. During the purification, when the ionic liquid contains impurities or is denatured, the purification performance thereof may deteriorate, and thus there is a need for a novel ionic liquid or a high-purity purification process.

However, high-purity purification of the ionic liquid requires an additional purification system and method, considerably increasing processing costs, which is undesirable.

Therefore, it is necessary to develop a novel technique for purifying an ionic liquid, which contains impurities or is denatured, to high purity in a simple manner and reusing the same.

SUMMARY

With the aim of solving the problems encountered in the related art, the present inventors have studied and ascertained that a discolored ionic liquid is capable of being decolored, thus culminating in the present invention.

Accordingly, an object of the present invention is to provide a method of decoloring an ionic liquid, which is discolored due to heat treatment upon purification, in a simple manner.

Another object of the present invention is to provide a method of decoloring an ionic liquid, which is discolored and is thus difficult to apply to the purification of an organic material, in a simple manner to thus be reused in the form of a high-purity ionic liquid.

The objects of the present invention are not limited to the foregoing, and other objects not mentioned herein will be able to be clearly understood by those skilled in the art from the following description.

In order to accomplish the above objects, the present invention provides a method of decoloring an ionic liquid, comprising preparing a discolored ionic liquid and decoloring the discolored ionic liquid through irradiation with UV rays.

In a preferred embodiment, the ionic liquid includes at least one cation selected from among cations represented by Chemical Formula 1 below.

[Chemical Formula 1]

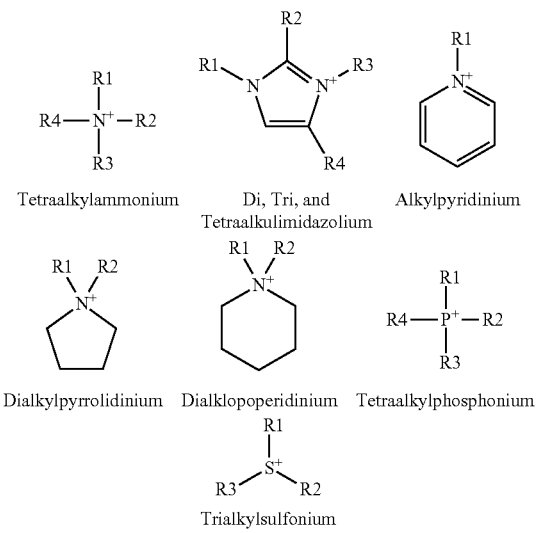

(wherein R1, R2, R3 and R4 are each a linear or branched alkyl group having n carbon atoms)

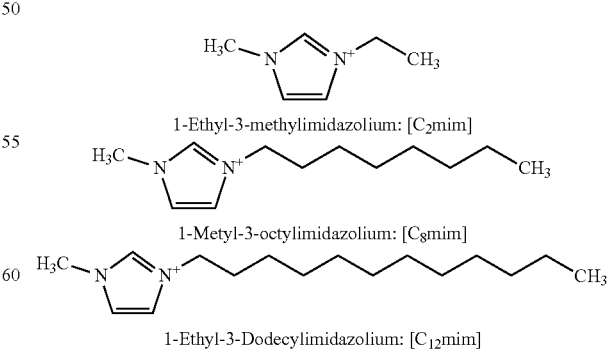

In a preferred embodiment, the ionic liquid includes at least one anion selected from among Cl$^-$, Br$^-$, NO$_3^-$, BF$_4^-$, PF$_6^-$, AlCl$_4^-$, Al$_2$Cl$_7^-$, AcO$^-$, CH$_3$COO$^-$, CF$_3$COO$^-$, $CH_3SO_3^-$, $CF_3SO_3^-$, $(CF_3SO_2)_2N^-$, $(CF_3SO_2)_3C^-$, $(CF_3CF_2SO_2)_2N^-$, $C_4F_9SO_3^-$, $C_3F7COO^-$, $(CF_3SO_2)(CF_3CO)N^-$, $C_4F_{10}N^-$, $C_2F_6NO_4S_2^-$, $C_2F_6NO_6S_2^-$, $C_4F_{10}NO_4S_2^-$, $CF_3SO_2^-$, $CF_3SO_3^-$, $C_4F_9SO_2^-$, $C_4F_9SO_3^-$, $PF_6^-$, $C_2H_6NO_4S_2^-$, $C_3F_6NO_3S^-$, $(CF_3SO_2)_2N^-$, and $CH_3CH(OH)CO_2^-$.

In a preferred embodiment, the decoloring the discolored ionic liquid is performed by irradiating the discolored ionic liquid with UV rays in a UV range corresponding to an absorption wavelength of the cation contained in the ionic liquid before discoloration.

In a preferred embodiment, the preparing the discolored ionic liquid is performed using an ionic liquid that is discolored due to heat treatment.

The present invention has the following superior effects.

A method of decoloring an ionic liquid according to the present invention is effective because an ionic liquid, which is discolored due to heat treatment upon purification, can be decolored in a simple manner.

Also, the method of decoloring an ionic liquid according to the present invention is effective because an ionic liquid, which is discolored and is thus difficult to apply to the purification of an organic material, can be decolored in a simple manner and can thus be reused in the form of a high-purity ionic liquid.

BRIEF DESCRIPTION OF THE DRAWINGS

FIG. 2 is of photographs showing changes in the colors of ionic liquids due to heat treatment;

DETAILED DESCRIPTION

Figure 1:
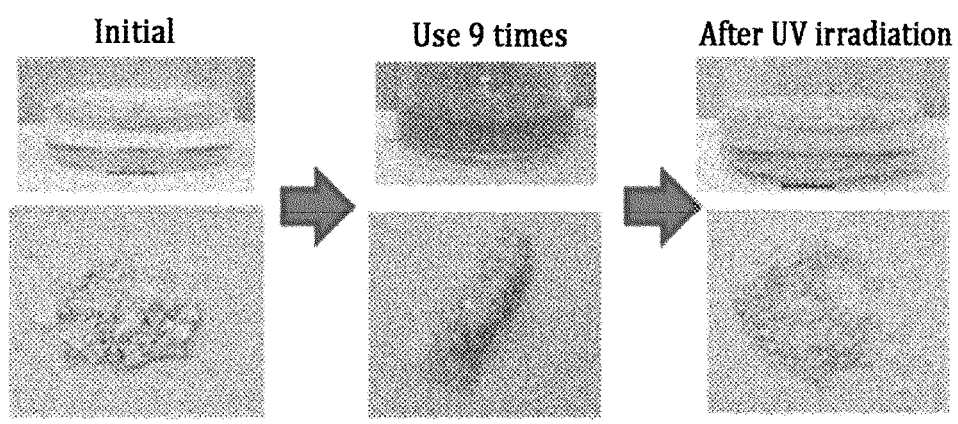
FIG. 1 is of photographs showing the process of decoloring a discolored ionic liquid used for the purification of an organic material.

Although the terms used in the present invention are selected from among generally known and used terms, some of the terms mentioned in the description of the present invention have been selected by the applicant, the detailed meanings of which should be understood not simply by the actual terms used but by the meaning of each term in the context of the detailed description of the invention or in consideration of the meanings used.

Hereinafter, a detailed description will be given of the technical configuration of the present invention with reference to preferred embodiments illustrated in the appended drawings.

However, the present invention is not limited to the embodiments described herein, and may be embodied in other forms. Like reference numerals used to describe the present invention throughout the specification denote like elements.

An embodiment of the present invention addresses a method of decoloring an ionic liquid, comprising preparing a discolored ionic liquid and decoloring the discolored ionic liquid through irradiation with UV rays.

The ionic liquid is a salt composed of an organic cation of a hetero ring and an inorganic anion.

The cation may be at least one selected from among cations represented by Chemical Formula 1 below.

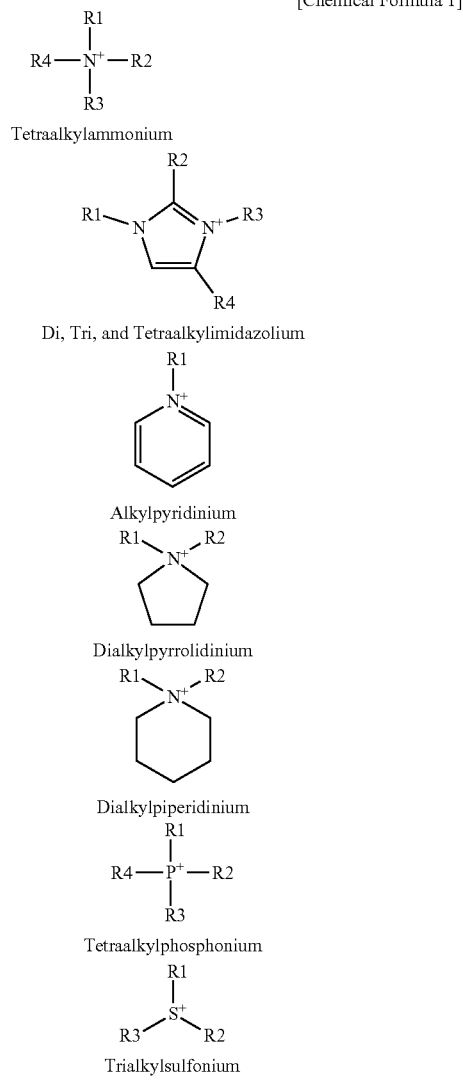

[Chemical Formula 1]

Tetraalkylammonium

Di, Tri, and Tetraalkylimidazolium

Alkylpyridinium

Dialkylpyrrolidinium

Dialkylpiperidinium

Tetraalkylphosphonium

Trialkylsulfonium (wherein R1, R2, R3 and R4 are each a linear or branched alkyl group having n carbon atoms)

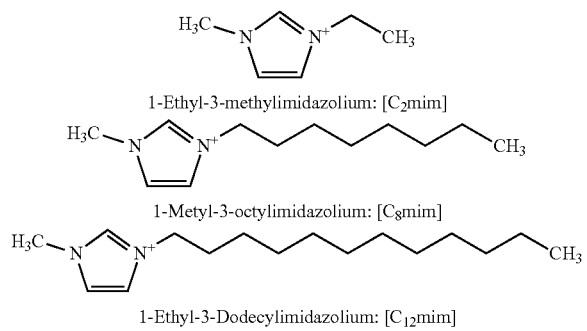

1-Ethyl-3-methylimidazolium: [C$_2$mim]

1-Metyl-3-octylimidazolium: [C$_8$mim]

1-Ethyl-3-Dodecylimidazolium: [C$_{12}$mim]

The anion may be at least one selected from among $Cl^-$, $Br^-$, $NO_3^-$, $BF_4^-$, $PF_6^-$, $AlCl_4^-$, $Al_2Cl_7^-$, $AcO^-$, $CH_3COO^-$, $CF_3COO^-$, $CH_3SO_3^-$, $CF_3SO_3^-$, $(CF_3SO_2)_2N^-$, $(CF_3SO_2)_3C^-$, $(CF_3CF_2SO_2)_2N^-$, $C_4F_9SO_3^-$, $C_3F7COO^-$, $(CF_3SO_2)(CF_3CO)N^-$, $C_4F_{10}N^-$, $C_2F_6NO_4S_2^-$, $C_2F_6NO_6S_2^-$, $C_4F_{10}NO_4S_2^-$, $CF_3SO_2^-$, $CF_3SO_3^-$, $C_4F_9SO_2^-$, $C_4F_9SO_3^-$, $PF_6^-$, $C_2H_6NO_4S_2^-$, $C_3F_6NO_3S^-$, $(CF_3SO_2)_2N^-$, and $CH_3CH(OH)\,CO_2^-$.

Here, examples of the ionic liquid used in an embodiment of the present invention include 1-ethyl-3-methylimidazolium bis(trifluoromethanesulfonyl)imide [$C_2$mim][TFSI] (Iolitec Co., 99%), 1-methyl-3-octylimidazolium bis(trifluoromethanesulfonyl)imide [$C_8$mim][TFSI] (Iolitec Co., 99%), and 1-dodecyl-3-methylimidazolium bis(trifluoromethanesulfonyl)imide [$C_{12}$mim][TFSI] (Iolitec Co. 98%), made using a hydrophobic anion TFSI$^-$ and three kinds of imidazole-based cations having different alkyl chain lengths.

The ionic liquid may be used to synthesize a material or to purify an organic material. When the ionic liquid is used to purify an organic material, heat treatment is carried out in a predetermined temperature range, and the ionic liquid is increasingly discolored with an increase in the number of purification processes.

The viscosity of the discolored ionic liquid varies depending on the extent of discoloration, and the viscosity increases with an increase in the discoloration. In the case where the discolored ionic liquid is used, it affects the material to be purified during the purification, and thus the purity thereof decreases, making it difficult to form a crystal phase.

When the ionic liquid is repetitively used for the purification of the organic material, it is discolored, and thus a new ionic liquid has to be used, or the discolored ionic liquid has to be purified to high purity. However, in order to purify the ionic liquid to an initial high purity, an additional ionic liquid purification system and method is required, which will cost as much as the cost of synthesizing the initial ionic liquid.

Hence, in an embodiment of the present invention, a discolored ionic liquid, particularly an ionic liquid discolored due to heat treatment, is decolored through irradiation with UV rays, thereby obtaining a high-purity ionic liquid, which may then be reused.

Here, in the decoloring process, a high decoloring effect is preferably exhibited upon irradiation with UV rays in a UV range corresponding to the absorption wavelength of the cation contained in the ionic liquid before discoloration.

For example, when [$C_{12}$mim] [TFSI] is used as the ionic liquid in an embodiment of the present invention, UV rays are preferably applied in the UV range (300 nm to 360 nm) corresponding to the intrinsic absorption wavelength (330 nm) of the cation contained in [$C_{12}$mim][TFSI] before discoloration.

FIG. 1 shows the process of decoloring a discolored ionic liquid used for the purification of an organic material.

With reference to FIG. 1, the initial color of the ionic liquid before use for the purification of an organic material is close to colorlessness. When such an ionic liquid is used several times for the purification of an organic material, it is discolored, and the ionic liquid is discolored to dark brown after nine purification processes. In an embodiment of the present invention, when the discolored ionic liquid is irradiated with UV rays in the UV range (306 nm) corresponding to the intrinsic absorption wavelength of the cation contained in the ionic liquid before discoloration, it can be seen to be decolored close to colorlessness.

TABLE 1

| Conditions | Purity (HPLC) % |
|---|---|
| Initial | 99.5 |
| Use 9 times for purification | 81 |
| UV irradiation (306 nm) | 98 |

[Table 1] shows changes in the purity of the initial ionic liquid, the discolored ionic liquid, and the ionic liquid after UV irradiation.

As is apparent from [Table 1], the purity (HPLC) of the initial ionic liquid before use for the purification of an organic material is 99.5%, but the purity of the discolored ionic liquid is 81% after use (9 times) for purification of the organic material, and thus the purity thereof is considerably lowered. However, in an embodiment of the present invention, the purity of the ionic liquid is increased to 98% through UV irradiation, which is close to the purity of the initial ionic liquid.

Consequently, in an embodiment of the present invention, the ionic liquid discolored due to heat treatment upon purification of an organic material is irradiated with UV rays in a wavelength range similar to the intrinsic absorption wavelength of the cation, and may thus be decolored. The high-purity ionic liquid may be manufactured at low cost in a simple manner, and may thus be reused.

EXAMPLE

Preparation of Reagent

As ionic liquids, 1-ethyl-3-methylimidazolium bis(trifluoromethanesulfonyl)imide [$C_2$mim][TFSI] (Iolitec Co., 99%), 1-methyl-3-octylimidazolium bis(trifluoromethanesulfonyl)imide [$C_8$mim][TFSI] (Iolitec Co., 99%), and 1-dodecyl-3-methylimidazolium bis(trifluoromethanesulfonyl)imide [$C_{12}$mim] [TFSI] (Iolitec Co. 98%) were prepared using a hydrophobic anion TFSI$^-$ and three kinds of imidazole-based cations having different alkyl chain lengths.

Discoloration Due to Heat Treatment

1000 μl of each of the ionic liquids [$C_2$mim][TFSI], [$C_8$mim][TFSI], and [$C_{12}$mim] [TFSI] was placed in a heating chamber, and changes in the color thereof depending on the temperature and atmosphere were observed. For heat treatment, the target temperature was set through TGA, and the temperature was elevated to 150° C., 200° C., and 250° C. at a rate of 5° C./min. When the temperature reached the target temperature, it was maintained for 1 hr and isothermal heat treatment was conducted, and cold working was performed in a heating chamber. The atmosphere was changed using $N_2$, $O_2$, and air, and purging was carried out at 200 ml/min from 1 hr before the test until all test procedures were completed.

Figure 2:
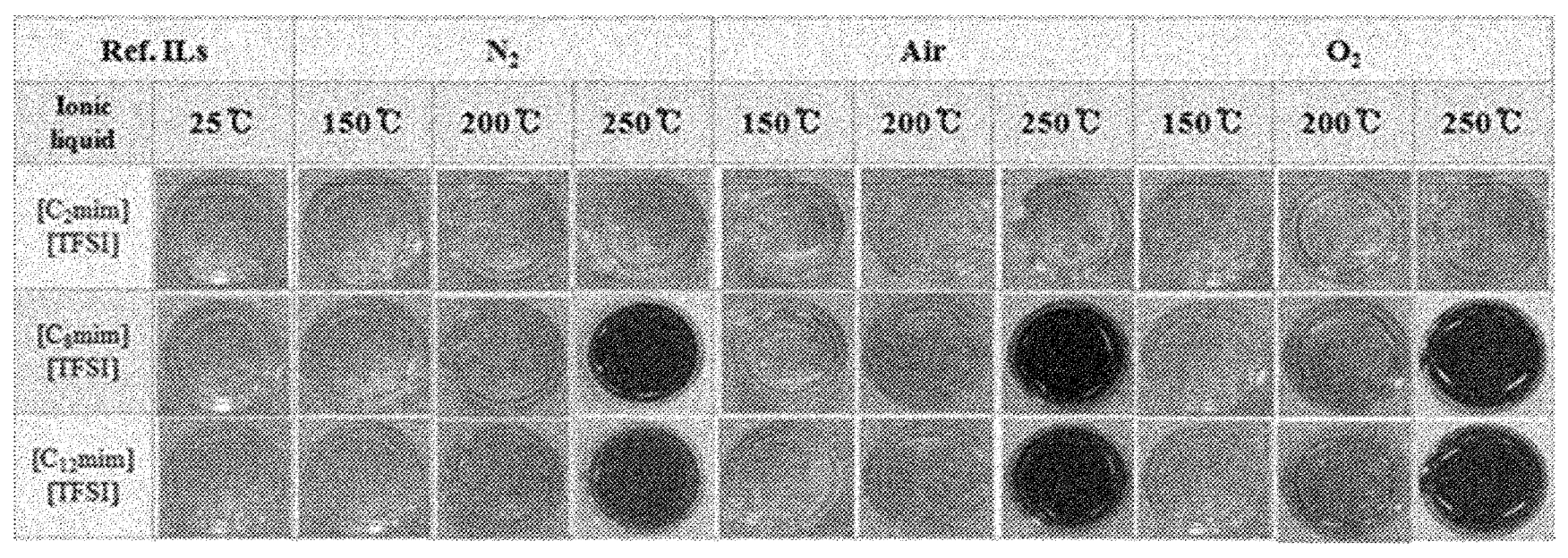

FIG. 2 is of photographs showing changes in the colors of the ionic liquids due to heat treatment.

With reference to FIG. 2, as the heat treatment temperature was higher, the color became dark in all of the tested ionic liquids. The colorless ionic liquid [$C_2$mim][TFSI] turned yellowish. The yellowish ionic liquids [$C_8$mim] [TFSI] and [$C_{12}$mim] [TFSI] turned dark brown. Based on the results of observation of color changes depending on the kind of ionic liquid, color changes were the lowest in [$C_2$mim] [TFSI] and the greatest in [$C_8$mim] [TFSI]. Also, based on the results of observation of color changes of the ionic liquid in different atmospheres, the color change of the ionic liquid that was heat treated in an $O_2$ atmosphere with high oxygen partial pressure was the greatest. This is interpreted to be because the color change of the ionic liquid is promoted due to a high extent of oxidation in the $O_2$ atmosphere, unlike the inert gas $N_2$.

Decoloring of Ionic Liquid

A decoloring test was performed using the [$C_{12}$mim][TFSI] ionic liquid prepared at 250° C. in the air of the above heat treatment process. The decoloring of the ionic liquid through irradiation with UV rays was performed in a dark room made of an acrylic box, and UV rays were applied at room temperature for 10 days using lamps of UV-C, having a main peak of 254 nm, UV-B, having a main peak of 306 nm, and UV-A, having a main peak of 352 nm.

Figure 3:
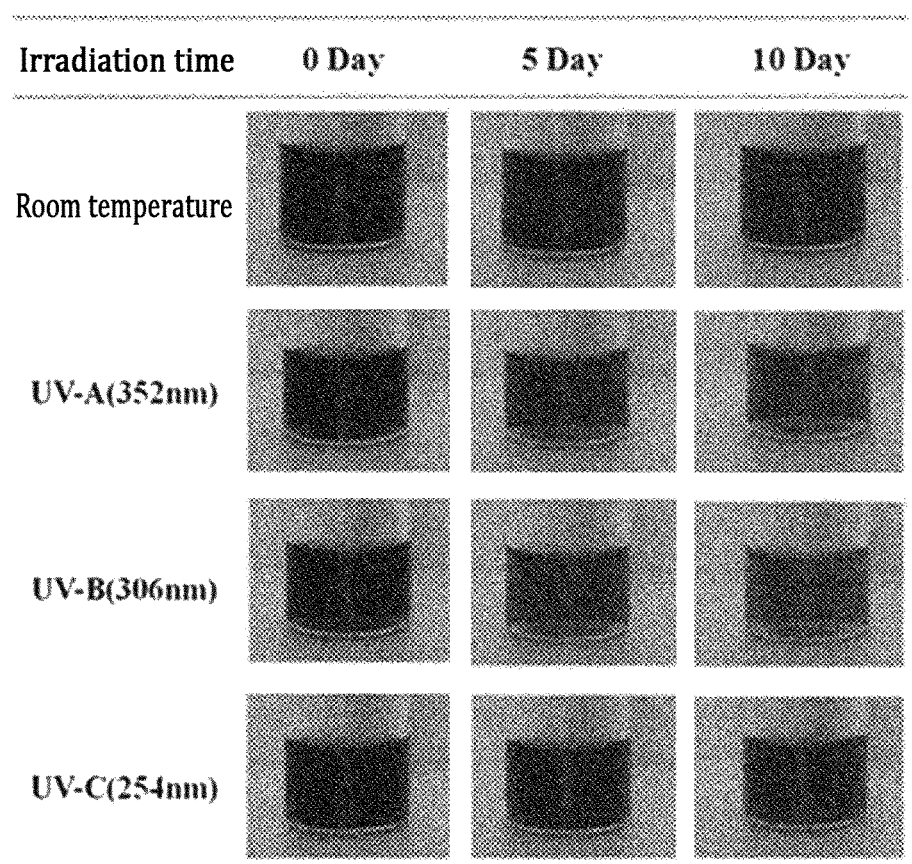
FIG. 3 is of photographs showing changes in the color of an ionic liquid through irradiation with UV rays according to an embodiment of the present invention.

FIG. 3 is of photographs showing color changes in the ionic liquid through irradiation with UV rays according to an embodiment of the present invention.

With reference to FIG. 3, when the ionic liquid ([$C_{12}$mim][TFSI]) discolored to dark brown due to heat treatment at 250° C. was maintained at room temperature for 10 days, there was almost no color change.

However, when UV rays were applied in the UV ranges of UV-B (306 nm) and UV-A (352 nm), corresponding to the intrinsic absorption wavelength (330 nm) of the cation contained in the ionic liquid ([$C_{12}$mim][TFSI]) before discoloration in an embodiment of the present invention, the color was changed to pale brown with an increase in UV irradiation time. The greater the number of intrinsic absorption wavelengths of the cation contained in the ionic liquid before discoloration, the greater the decoloring effect. This is interpreted to be because the structure of the cation is reversed by applying the UV rays corresponding to the absorption wavelength of the cation to thus decolor the ionic liquid. On the other hand, when UV rays were applied in the UV range of UV-C (254 nm), different from the intrinsic absorption wavelength of the cation, there was almost no decoloring effect.

Figure 4:
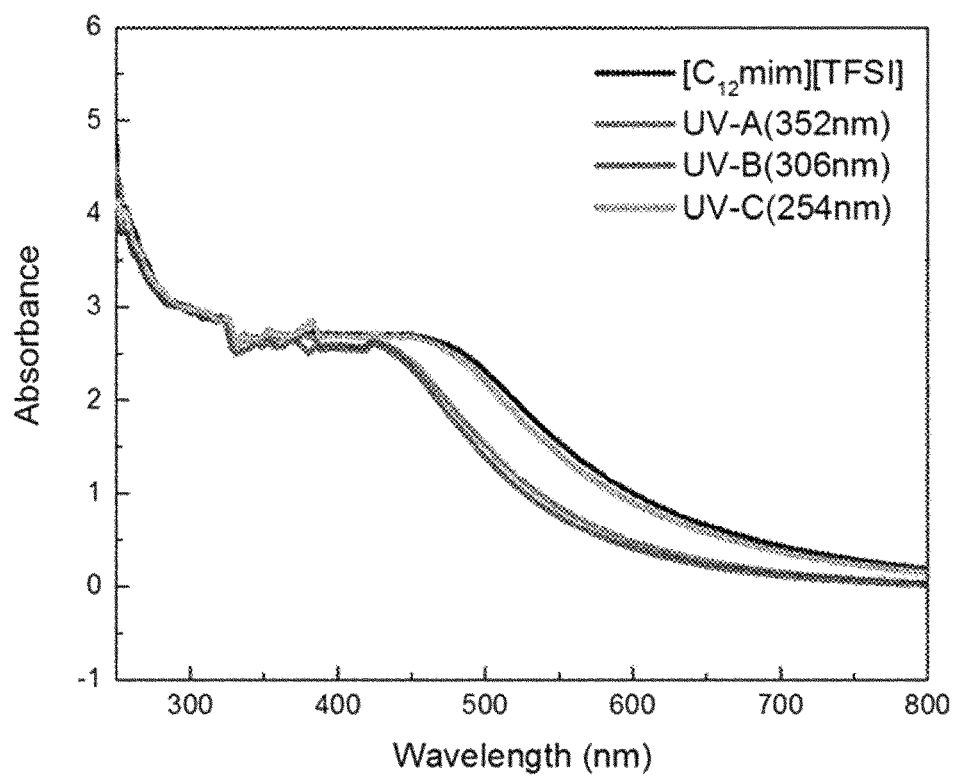
FIG. 4 is a graph showing the absorbance of the ionic liquid irradiated with UV rays according to an embodiment of the present invention.

FIG. 4 is a graph showing the absorbance of the ionic liquid irradiated with UV rays according to an embodiment of the present invention.

With reference to FIG. 4, based on the results of measurement of absorbance of [$C_{12}$mim][TFSI] irradiated with UV-Vis spectra, when UV rays were applied in the wavelength range of UV-C (254 nm), absorbance similar to that of the discolored ionic liquid was exhibited, and when UV rays were applied in the UV ranges of UV-B (306 nm) and UV-A (352 nm), absorbance was decreased.

Therefore, it can be considered that the ionic liquid was discolored to dark brown due to deprotonation at the C2-position of the cation, and was irradiated with the UV rays corresponding to the absorption wavelength of the cation, whereby the structure of the cation was reversed, and thus the color of the ionic liquid became pale (decoloration). The purity of the decolored ionic liquid was as high as 98%, as shown in [Table 1], which is similar to that of the initial ionic liquid.

Although the preferred embodiments of the present invention have been disclosed for illustrative purposes, those skilled in the art will appreciate that various modifications and substitutions are possible, without departing from the scope and spirit of the invention as disclosed in the accompanying claims.

According to the present invention, the method of decoloring the ionic liquid can be employed in ionic liquid purification fields, and cost reduction becomes possible because of reuse of the ionic liquid. Such an ionic liquid can be utilized in a variety of industrial fields, including those of secondary battery electrolytes, catalysts, liquid-liquid extraction solvents, carbon dioxide capture, thermal fluids, and the like.

The invention claimed is:
1. A method of decoloring an ionic liquid, comprising: preparing a discolored ionic liquid from an ionic liquid, wherein the discolored ionic liquid is prepared by using an ionic liquid for purifying an organic material, thereby making the ionic liquid contain impurities or denatured and therefore discolored; and decoloring the discolored ionic liquid through irradiation with UV rays.

2. The method of claim 1, wherein the ionic liquid includes at least one cation selected from the group consisting of cations represented by formulae below:

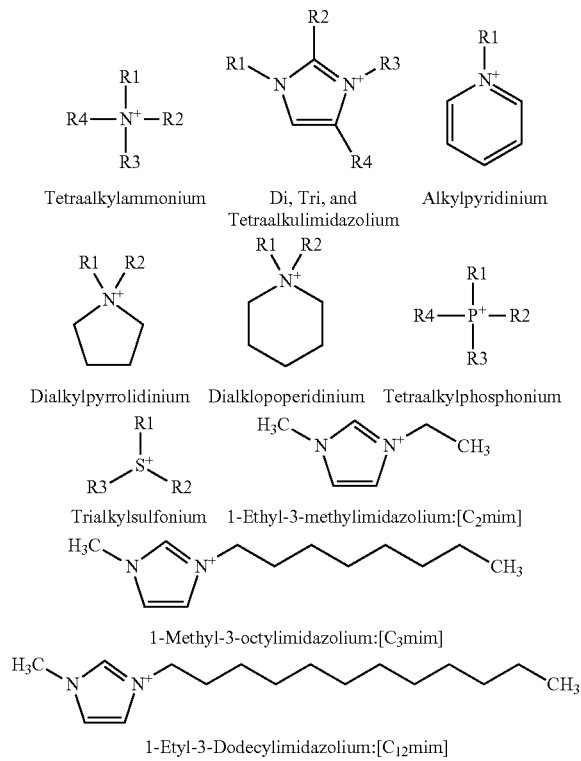

wherein R1, R2, R3 and R4 are each independently a linear or branched alkyl group.

3. The method of claim 2, wherein the ionic liquid includes at least one anion selected from the group consisting of $Cl^-$, $Br^-$, $NO_3^-$, $BF_4^-$, $PF_6^-$, $AlCl_4^-$, $Al_2Cl_7^-$, $AcO^-$, $CH_3COO^-$, $CF_3COO^-$, $CH_3SO_3^-$, $CF_3SO_3^-$, $(CF_3SO_2)_2N^-$, $(CF_3SO_2)_3C^-$, $(CF_3CF_2SO_2)_2N^-$, $C_4F_9SO_3^-$, $C_3F7COO^-$, $(CF_3SO_2)(CF_3CO)N^-$, $C_4F_{10}N^-$, $C_2F_6NO_4S_2^-$, $C_2F_6NO_6S_2^-$, $C_4F_{10}NO_4S_2^-$, $CF_3SO_2^-$, $CF_3SO_3^-$, $C_4F_9SO_2^-$, $C_4F_9SO_3^-$, $PF_6^-$, $C_2H_6NO_4S_2^-$, $C_3F_6NO_3S^-$, $(CF_3SO_2)_2N^-$, and $CH_3CH(OH)CO_2^-$.

4. The method of claim 3, wherein the decoloring of the discolored ionic liquid is performed by irradiating the discolored ionic liquid with the UV rays in a UV range corresponding to an absorption wavelength of the cation contained in the ionic liquid before discoloration.

5. The method of claim 2, wherein the decoloring of the discolored ionic liquid is performed by irradiating the discolored ionic liquid with the UV rays in a UV range corresponding to an absorption wavelength of the cation contained in the ionic liquid before discoloration.

6. The method of claim 1, wherein the decoloring of the discolored ionic liquid is performed by irradiating the discolored ionic liquid with the UV rays in a UV range corresponding to an absorption wavelength of a cation contained in the ionic liquid before discoloration.

* * * * *